(12) United States Patent
Foley et al.

(10) Patent No.: US 8,470,601 B2
(45) Date of Patent: Jun. 25, 2013

(54) APPARATUS AND METHOD FOR INDICATING BIOLOGICAL CONTENT WITHIN A CONTAINER

(75) Inventors: Tony Foley, Manchester, NH (US); Gary T. Dane, Bow, NH (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 0 days.

(21) Appl. No.: 13/297,427

(22) Filed: Nov. 16, 2011

(65) Prior Publication Data

US 2012/0122226 A1    May 17, 2012

Related U.S. Application Data

(60) Provisional application No. 61/414,100, filed on Nov. 16, 2010.

(51) Int. Cl.
*G01N 31/22* (2006.01)
*A61L 2/28* (2006.01)

(52) U.S. Cl.
USPC .............. 436/1; 422/1; 422/7; 422/9; 422/11; 422/26; 422/27; 422/28

(58) Field of Classification Search
USPC .................. 422/1, 7, 9, 11, 26–28; 436/1
See application file for complete search history.

(56) References Cited

U.S. PATENT DOCUMENTS

| | | | | |
|---|---|---|---|---|
| 3,661,717 A * | 5/1972 | Nelson | ............................. | 435/31 |
| 3,747,751 A * | 7/1973 | Miller et al. | .................. | 206/277 |
| 3,844,275 A * | 10/1974 | Elliott | ............................. | 600/345 |
| 3,942,467 A * | 3/1976 | Witonsky | ........................ | 116/207 |
| 3,960,670 A * | 6/1976 | Pflug | ................................ | 435/31 |
| 3,991,881 A * | 11/1976 | Augurt | ........................... | 206/439 |
| 4,049,121 A * | 9/1977 | White | ............................ | 206/439 |
| 4,098,577 A * | 7/1978 | Halpern | ............................ | 436/1 |
| 4,121,714 A * | 10/1978 | Daly et al. | ..................... | 206/363 |
| 4,168,779 A * | 9/1979 | Yokokoji et al. | ............... | 206/439 |
| 4,206,844 A * | 6/1980 | Thukamoto et al. | ........... | 206/439 |
| 4,291,122 A * | 9/1981 | Orelski | ............................ | 435/31 |
| 4,311,793 A * | 1/1982 | Halleck | ............................ | 435/31 |
| 4,325,254 A * | 4/1982 | Svacina et al. | ................ | 607/114 |
| 4,448,548 A * | 5/1984 | Foley | .................................. | 374/160 |
| 4,539,929 A * | 9/1985 | Sestak et al. | ................... | 116/221 |
| 4,562,047 A * | 12/1985 | Sestak et al. | ................... | 422/300 |
| 4,596,773 A * | 6/1986 | Wheeler, Jr. | ..................... | 435/31 |
| 4,612,872 A * | 9/1986 | Whelchel et al. | .............. | 116/218 |
| 4,671,943 A * | 6/1987 | Wahlquist | ...................... | 422/300 |
| 4,732,850 A * | 3/1988 | Brown et al. | .................... | 435/31 |
| 4,783,321 A * | 11/1988 | Spence | .......................... | 422/300 |

(Continued)

FOREIGN PATENT DOCUMENTS

WO        2010045138 A2    4/2010

*Primary Examiner* — Arlen Soderquist
(74) *Attorney, Agent, or Firm* — Hayes Soloway P.C.

(57) ABSTRACT

An apparatus for indicating biological content within a container is provided. The apparatus includes a medical sterilization container having a cover removably attached to the medical sterilization container. An enclosable, sterilizable interior compartment is formed by the medical sterilization container and the cover, wherein the interior compartment is sized to house at least one medical instrument. A biological indicator is located at least partially in communication with the interior compartment, wherein the biological indicator provides at least one indication of biological content within the interior compartment after the medical sterilization container and cover are subjected to a sterilization process.

20 Claims, 6 Drawing Sheets

U.S. PATENT DOCUMENTS

| | | | |
|---|---|---|---|
| 4,850,716 A * | 7/1989 | Baker et al. | 374/160 |
| 5,066,464 A * | 11/1991 | Augurt | 422/414 |
| 5,225,162 A * | 7/1993 | Scoville | 422/401 |
| 5,344,017 A * | 9/1994 | Wittrock | 206/459.1 |
| 5,372,787 A * | 12/1994 | Ritter | 422/119 |
| 5,405,580 A * | 4/1995 | Palmer | 422/28 |
| 5,508,006 A * | 4/1996 | Gabele et al. | 422/119 |
| 5,552,320 A * | 9/1996 | Smith | 435/287.4 |
| 5,565,634 A * | 10/1996 | Graessle et al. | 73/865.9 |
| 5,620,656 A * | 4/1997 | Wensky et al. | 422/28 |
| 5,739,004 A * | 4/1998 | Woodson | 435/31 |
| 5,745,039 A * | 4/1998 | Hof et al. | 340/590 |
| 5,770,393 A * | 6/1998 | Dalmasso et al. | 435/31 |
| 5,801,010 A * | 9/1998 | Falkowski et al. | 435/31 |
| 5,830,683 A * | 11/1998 | Hendricks et al. | 435/31 |
| 5,834,313 A * | 11/1998 | Lin | 436/1 |
| 5,922,592 A * | 7/1999 | Tautvydas | 435/287.4 |
| 5,942,408 A * | 8/1999 | Christensen et al. | 435/31 |
| 6,166,538 A * | 12/2000 | D'Alfonso | 324/228 |
| 6,218,189 B1 * | 4/2001 | Antonoplos et al. | 436/1 |
| 6,534,006 B2 | 3/2003 | Hehenberger | |
| 7,091,042 B2 * | 8/2006 | Lemus et al. | 436/1 |
| 7,122,150 B2 | 10/2006 | Gonzalez et al. | |
| 7,993,602 B2 * | 8/2011 | Moriyama et al. | 422/292 |
| 2003/0213715 A1 | 11/2003 | Klepac et al. | |

\* cited by examiner

APPARATUS AND METHOD FOR INDICATING BIOLOGICAL CONTENT WITHIN A CONTAINER

CROSS REFERENCE TO RELATED APPLICATION

This application claims benefit of U.S. Provisional Application Ser. No. 61/414,100, entitled, "Apparatus and Method for Indicating Biological Content within a Container," filed Nov. 16, 2010, the entire disclosure of which is incorporated herein by reference.

FIELD OF THE DISCLOSURE

The present disclosure is generally related to a medical sterilization container and more particularly is related to an apparatus and method for indicating biological content within a container.

BACKGROUND OF THE DISCLOSURE

Articles such as medical instruments and the like are usually sterilized in a sterilization machine, such as an autoclave, in which the articles are exposed to high-pressure saturated steam for a relatively brief interval. Unless the articles are to be used immediately and in close proximity to the autoclave, it is desirable to sterilize the articles while they are inside a sterilization container. Once the sterilization process is complete, the medical instruments may be housed within the sterilization container until they are used for a medical procedure. To ensure a safe medical environment, medical staff must ensure that the medical instruments are fully sterilized and that the sterilization container hasn't become contaminated since the sterilization process. However, it is difficult if not impossible to tell when a sterilized container has subsequently been opened, thereby rendering any medical instruments inside contaminated and unfit for a medical procedure.

Thus, a heretofore unaddressed need exists in the industry to address the aforementioned deficiencies and inadequacies.

SUMMARY OF THE DISCLOSURE

Embodiments of the present disclosure provide an apparatus and method for indicating biological content within a container. Briefly described, in architecture, one embodiment of the apparatus, among others, can be implemented as follows. The apparatus includes a medical sterilization container having a cover removably attached to the medical sterilization container. An enclosable, sterilizable interior compartment is formed by the medical sterilization and the cover. The interior compartment is sized to house at least one medical instrument. A biological indicator located at least partially in communication with the interior compartment, wherein the biological indicator provides at least one indication of biological content within the medical sterilization container after the medical sterilization container and cover are subjected to a sterilization process.

The present disclosure can also be viewed as providing methods for indicating biological content within a container. In this regard, one embodiment of such a method, among others, can be broadly summarized by the following steps: subjecting a medical sterilization container having a cover removably attached to the medical sterilization container to a sterilization process, wherein the medical sterilization container has an enclosable, sterilizable interior compartment formed by the medical sterilization container and the cover, wherein the interior compartment is sized to house at least one medical instrument; and indicating with the biological indicator located at least partially in communication with the interior compartment a presence of a biological content within the interior compartment after a completion of the sterilization process.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
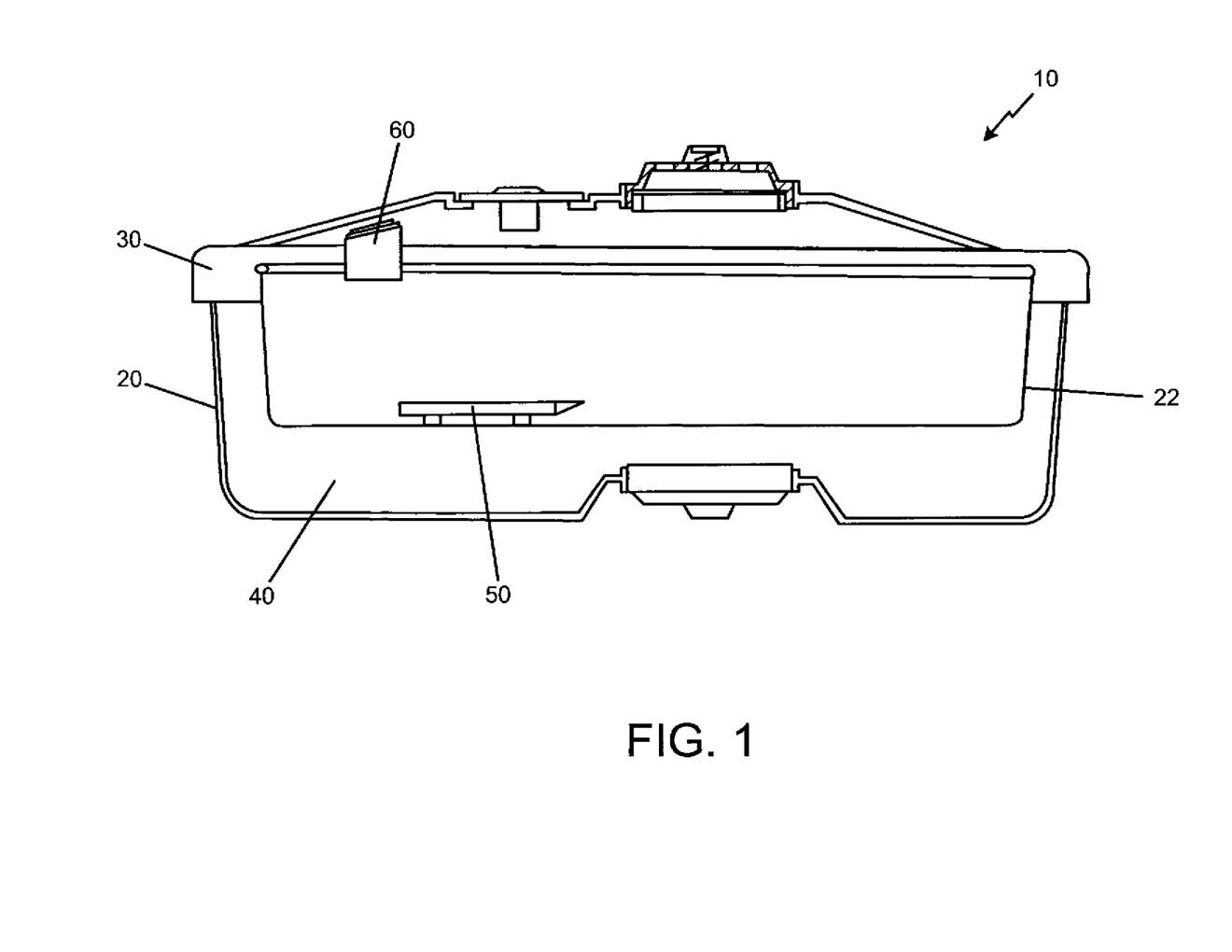
FIG. 1 is a cross-sectional illustration of an apparatus for indicating biological content within a container, in accordance with a first exemplary embodiment of the present disclosure.

FIG. 1 is a cross-sectional illustration of an apparatus for indicating biological content within a container 10, in accordance with a first exemplary embodiment of the present disclosure. The apparatus for indicating biological content within a container 10, which may be referred to simply as 'apparatus 10' includes a medical sterilization container 20 having a cover 30 that is removably attached to the medical sterilization container 20. An enclosable, sterilizable interior compartment 40 is formed by the medical sterilization container 20 and the cover 30. The interior compartment 40 is sized to house at least one medical instrument 50. A biological indicator 60 is located at least partially in communication with the interior compartment 40. The biological indicator 60 provides at least one indication of biological content within the interior compartment 40 after the medical sterilization container 20 and cover 30 are subjected to a sterilization process.

The medical sterilization container 20 may include any container that has an enclosable interior compartment 40, which is usually provided through the use of the cover 30. However, the medical sterilization container 20 may be capable of having an enclosed interior compartment 40 without the use of a cover 30, or similar structure. The medical sterilization container 20 is sized and designed to be used in a sterilization environment, such as by inserting the medical sterilization container 20 into an external autoclave, or other sterilizing device. While in the autoclave, the medical sterilization container 20 may be subjected to heat, pressure, chemicals, or other means of sterilization. The medical sterilization container 20 may also function with a sterilization medium that is placed within an interior compartment of the medical sterilization container 20. The interior compartment may include the interior compartment 40 of the medical sterilization container 20, or it may include another portion of the medical sterilization container 20.

The interior compartment 40 may be characterized as the area of the medical sterilization container 20 that is interior of the walls of the medical sterilization container 20 and the cover 30, when the cover 30 is affixed to the medical sterilization container 20. As is shown in FIG. 1, the interior compartment 40 may be sized to hole a tray 22 for supporting the quantity of medical instruments 50, or any portion thereof, while inside the medical sterilization container 20. The interior compartment 40 may be sized to allow for sufficient space around a tray 22, thereby allowing for sterilization material to contact various portions of the tray 22. For example, the tray 22 may include perforations for allowing sterilization material to pass through, and it may have a plurality of holding devices, such as flexible protrusions, formed shapes, or other holders that can receive a medical instrument 50. The holding devices may be capable of substantially securing the medical instrument 50 before, during, and after a sterilization process, while at the same time, providing enough space proximate to the medical instrument 50 to allow for proper sterilization. Of course, the medical sterilization container 20 may be capable of holding a quantity of medical instruments 50 during a sterilization process and retaining the sterilized environment within the interior compartment 40 after the sterilization process is completed without the use of a tray 22 or similar structure.

Any number of biological indicators 60 may be used with a single apparatus 10, but it may be preferable to use only one biological indicator 60 with each apparatus 10 to lessen the costs associated with the biological indicators 60. The biological indicator 60 may be positioned in communication with the interior compartment 40 of the medical sterilization container 20. This may include any position where the biological indicator 60, or a component or portion of the biological indicator 60, is in contact with the interior compartment 40 of medical sterilization container 20. This positioning of the biological indicator 60 allows for proper sensing and/or indicating a biological content within the interior compartment 40. The biological indicator 60 may be positioned within any type of structure, such as a mesh basket, perforated container, holding device, adhesively-bonded device, or any combination thereof.

As one having skill in the art can see, many variations on the exact location of the biological indicator 60 exists. For example, the biological indicator 60 may be fully located within the interior compartment 40, partially located within the interior compartment 40, positioned within the cover 30, within a side wall of the medical sterilization container 20, and any combination thereof. As is shown in FIG. 1, the biological indicator 60 is positioned fully within the medical sterilization container 20, proximately below the cover 30. The biological indicator 60 may also be positioned such that it may be removed from its positioned in communication with the interior compartment 40 without opening the cover 30, and therefore, without subjecting the interior compartment 40 to contamination or unsterile conditions. Other variations may include an electronic-based biological indicator 60, such as an electronic sterility indicator, that has a transmitter positioned within the interior compartment 40 and a receiver positioned exterior of the medical sterilization container 20 (the receiver is not shown in FIG. 1).

Figure 2:
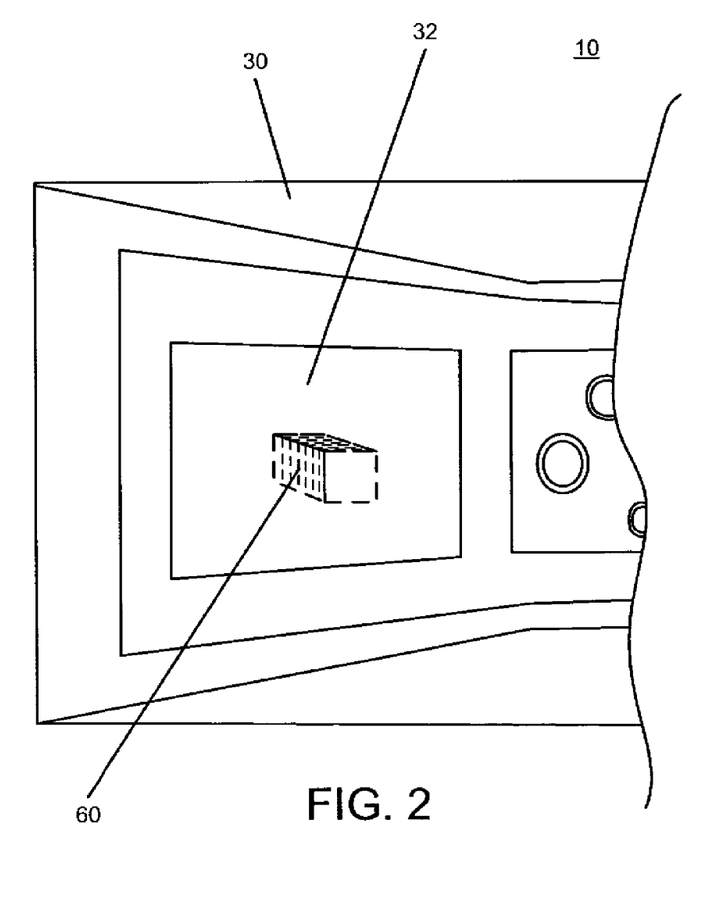
FIG. 2 is a top view illustration of the apparatus for indicating biological content within a container of FIG. 1, in accordance with the first exemplary embodiment of the present disclosure.

FIG. 2 is a top view illustration of the apparatus for indicating biological content within a container of FIG. 1, in accordance with the first exemplary embodiment of the present disclosure. In particular, FIG. 2 illustrates a top view of the cover 30 of the medical sterilization container 20 that depicts a materially translucent portion 32 within the cover 30. The materially translucent portion 32 may allow a user of the apparatus 10 to view an object within the interior compartment 40 of the medical sterilization container 20 while the cover 30 is positioned on the medical sterilization container 20. Accordingly, the materially translucent portion 32 may be positioned within the cover 30, within the medical sterilization container 20, or within another component of the apparatus 10. For example, the materially translucent portion 32 may allow a user of the medical sterilization container 20 to view a biological indicator 60 within the interior compartment 40 after the medical sterilization container 20 has been subjected to a sterilization process. This permits the user to identify the biological content within the interior compartment 40 without having to remove the cover 30 or otherwise subject the medical instruments 50 within the medical sterilization container 20 to an unsterile environment.

The materially translucent portion 32 may be constructed from any material that provides a substantially non-opaque viewing window through the cover 30. For example, the materially translucent portion 32 may include a material that is substantially or fully translucent, transparent, and/or clear, thereby allowing enough light to traverse through the materially translucent portion 32 for a user external to the apparatus 10 to see through the materially translucent portion 32. Any degree of viewing through the materially translucent portion 32 is considered within the scope of the present disclosure. Commonly, the materially translucent portion 32 may be integrally constructed with the cover 30, or otherwise connected to the cover 30 to allow for a substantially unitary construction. Of course, the materially translucent portion 32 may be designed to be openable, removable, replaceable, or otherwise capable of being manipulated or altered, depending on the design of the apparatus 10.

The biological indicator 60 may include any type of indicator device that is capable of indicating any biological content within the interior compartment 40. This may include sophisticated electronic devices, simple chemical-based devices, or a variety of other devices, or any combination thereof. For example, the biological indicator 60 may include indicator strip, such as the 3M® Attest® biological indicator, or any other type of indicator strip. The indicator strip may be positioned fully within the interior compartment 40 but may be viewable from outside of the medical sterilization container 20 by the materially translucent portion 32 in the medical sterilization container 20 or the cover 30.

The biological indicator 60 may also include an indicator label, such as a temperature indicating label like the Tempilable® label sold by the Tempil Corporation. This temperature indicating label may be positioned fully within the interior compartment 40 and may be viewable from outside of the medical sterilization container 20 by the materially translucent portion 32 in the medical sterilization container 20 or the cover 30. The temperature indicator label may indicate when a specific temperature is reached within the interior compartment 40 during a sterilization process. The specific temperature may be one, which eliminates all biological content from within the interior compartment 40. Accordingly, when the sterilization process is completed, the temperature indicator strip may indicate that the temperature has been reached and the interior compartment is sterile.

Figure 3:
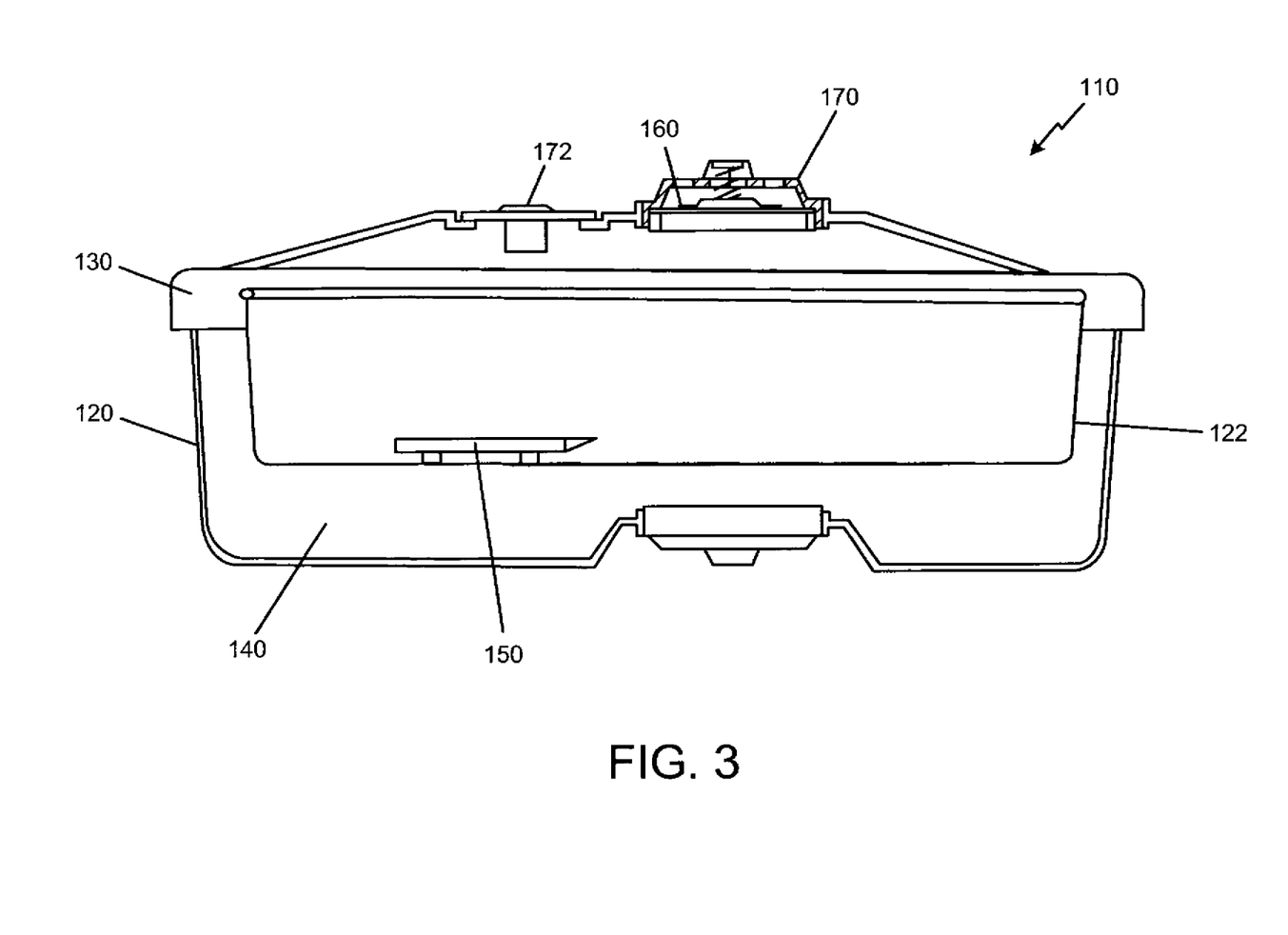
FIG. 3 is a cross-sectional illustration of an apparatus for indicating biological content within a container, in accordance with a second exemplary embodiment of the present disclosure.

FIG. 3 is a cross-sectional illustration of an apparatus for indicating biological content within a container 110, in accordance with a second exemplary embodiment of the present disclosure. The apparatus for indicating biological content within a container 110 of the second exemplary embodiment, which may be referred to herein as 'apparatus 110' may be substantially similar to the apparatus 10 of the first exemplary embodiment, and include any of the features, designs and/or configurations that are described with respect to the first exemplary embodiment. As is illustrated, the apparatus 110 includes a medical sterilization container 120 having a cover 130 that is removably attached to the medical sterilization container 120. An enclosable, sterilizable interior compartment 140 is formed by the medical sterilization container 120 and the cover 130. The interior compartment 140 is sized to house at least one medical instrument 150. As is shown, the at least one medical instrument 150 may be positioned on a tray 122 within the medical sterilization container 120.

In the second exemplary embodiment, the biological indicator 160 is depicted as being located within the cover 130; however, the biological indicator 160 may alternatively be located within a wall of the medical sterilization container 120, or another structure of the apparatus 110. Specifically, the biological indicator 160 is disclosed as including a pressure indicator having a flexible membrane, provides at least one indication of biological content within the interior compartment 140 after the medical sterilization container 120 and cover 130 are subjected to a sterilization process. The flexible membrane may be a component of a valve, or another structure of the apparatus 110. For example, a flexible membrane within the valve may be designed to indicate a specific temperature, pressure, or another characteristic indicative of a biological content within the medical sterilization container 120. This may include the use of a pressure-actuated valve having a shape-memory alloy (SMA) material or similar material that changes based on a temperature. In FIG. 3, the biological indicator 160 is illustrated as being integral with a SMA valve 170 within the cover 130. However, any number of secondary valves 172 may be included with the apparatus 110, wherein the biological indicator 160 is integral therewith.

In one of many alternatives, the flexible membrane of the biological indicator 160 may be an independent structure capable of indicating a specific temperature, pressure, or another characteristic indicative of a biological content within the medical sterilization container 120. The biological indicator 160 may be positioned within the cover 130 between the interior compartment 140 and exterior atmosphere. As the medical sterilization container 120 is subjected to a sterilization process, the pressure within the interior compartment 140 builds up. This pressure increase may deform the flexible membrane of the biological indicator 160 thereby altering its shape. The flexible membrane may be positioned proximate to a colored membrane that has at least one color. When the flexible membrane contacts the colored membrane, a second color may be formed from the contacting of the colored membrane by the flexible membrane. This second color may indicate that a pressure change has occurred within the interior compartment 140, which is an indication of a successful sterilization process.

Figure 4:
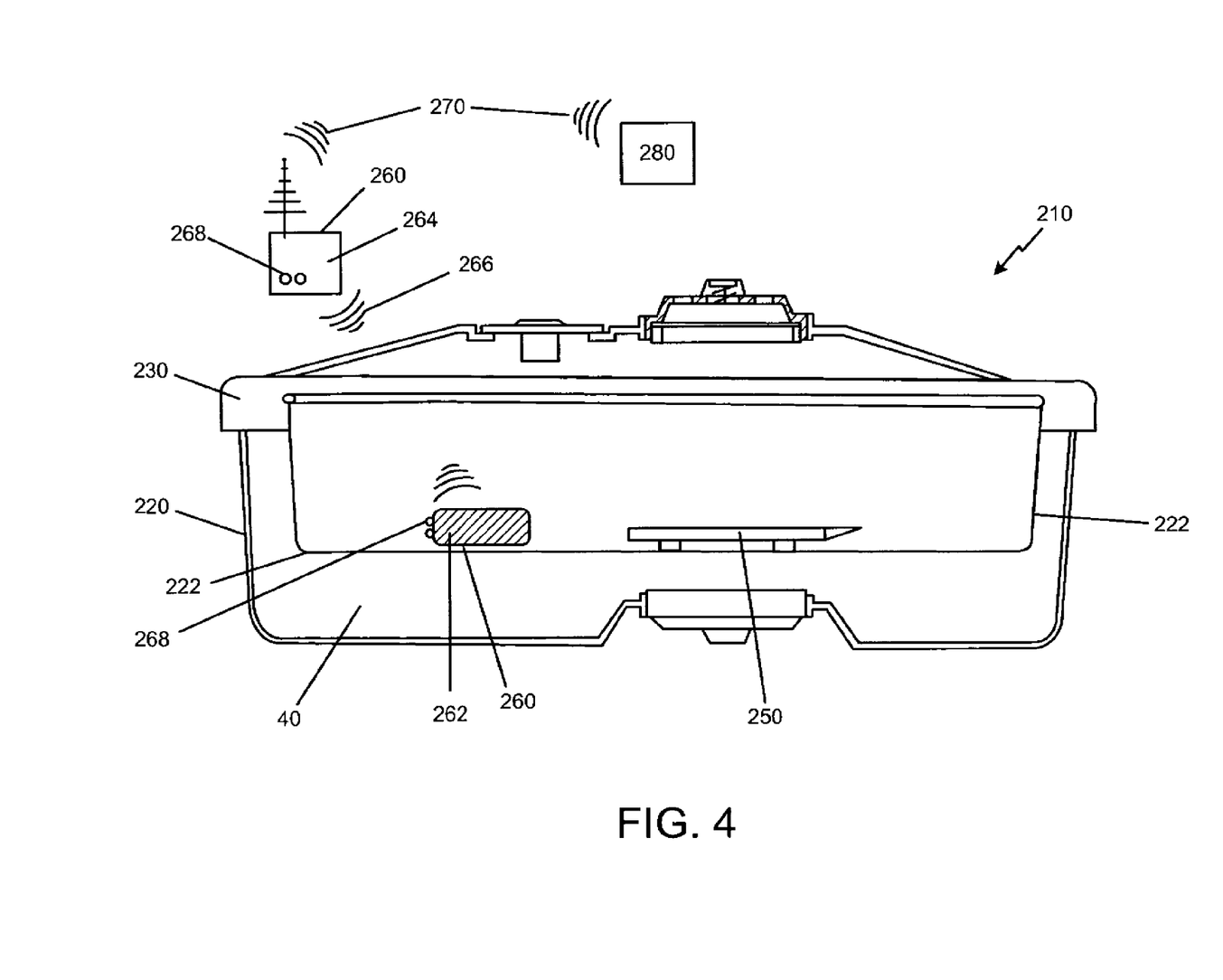
FIG. 4 is a cross-sectional illustration of an apparatus for indicating biological content within a container, in accordance with a third exemplary embodiment of the present disclosure.

FIG. 4 is a cross-sectional illustration of an apparatus for indicating biological content within a container 210, in accordance with a third exemplary embodiment of the present disclosure. The apparatus for indicating biological content within a container 210 of the third exemplary embodiment, which may be referred to herein simply as 'apparatus 210' may be substantially similar to the apparatus 10 and the apparatus 110 of the first and second exemplary embodiments, respectively, and include any of the features, designs and/or configurations that are described with respect to the first or second exemplary embodiments. As is illustrated, the apparatus 210 includes a medical sterilization container 220 having a cover 230 that is removably attached to the medical sterilization container 220. An enclosable, sterilizable interior compartment 240 is formed by the medical sterilization container 220 and the cover 230. The interior compartment 240 is sized to house at least one medical instrument 250, which may be positioned on or supported by a tray 222.

As is shown in FIG. 4, the biological indicator 260 may be located within the interior compartment 240 and provide an indication of a biological content within the interior compartment 240. The biological indicator 260 may include an electronic sterility indicator, or another type of electronic biological content indicator, which may include a transmitter 262 positioned within the interior compartment 240 and a receiver 264 positioned exterior of the medical sterilization container 220. One or more signals 266 may be transmitted between the transmitter 262 and the receiver 264. Thus, as can be seen, the biological indicator 260 may be located within and external to the medical sterilization container 220. The transmitter 262 may be positioned on any portion of the interior compartment 240, such as on a medical instrument tray 222, on another surface, affixed to or integral with the medical sterilization container 220 and/or the cover 230, or any combination thereof.

Accordingly, the electronic-based biological indicator 260 may sense a biological content within the interior compartment 240 and record data associated with the sensed biological content. The data may correspond to a monitored biological content, the sterilization process and a characteristic associated with the sterilization process, such as a sterilization temperature, a sterilization process duration time, a sterilization material, or any other relevant characteristic of the sterilization process. The data may be communicated between the transmitter 262 and receiver 264, and to any additional device, such as a computer or display screen (not shown). Any of the data collected by the electronic-based biological indicator 260 may be recorded, stored, filtered, or otherwise manipulated. For example, the biological indicator 260 may also record a log history of the sterilization of the medical sterilization container 220.

In addition to monitoring the biological content of the interior compartment 240, the biological indicator 260 may also provide data relating to its own functioning. This may include data indicating a battery life, the status of any computerized components including successful and unsuccessful processes and/or a signal status. The biological indicator 260 may include a plurality of lights 268, such as LED lights, on either the transmitter 262 and/or receiver 264. A green light, for example, may indicate a successful sterilization process and a red light indicates an unsuccessful sterilization process, or a non-sterile environment within the interior compartment 240. Furthermore, the biological indicator 260 may emit one or more signals 270 to a computerized device 280 to relay any monitored biological content outside of the apparatus 210. The biological indicator 260 may be designed to last for any number of uses, such as 100 cycles or more and may provide a time-lapse indication for any length of time, such as a few days or more.

Figure 5:
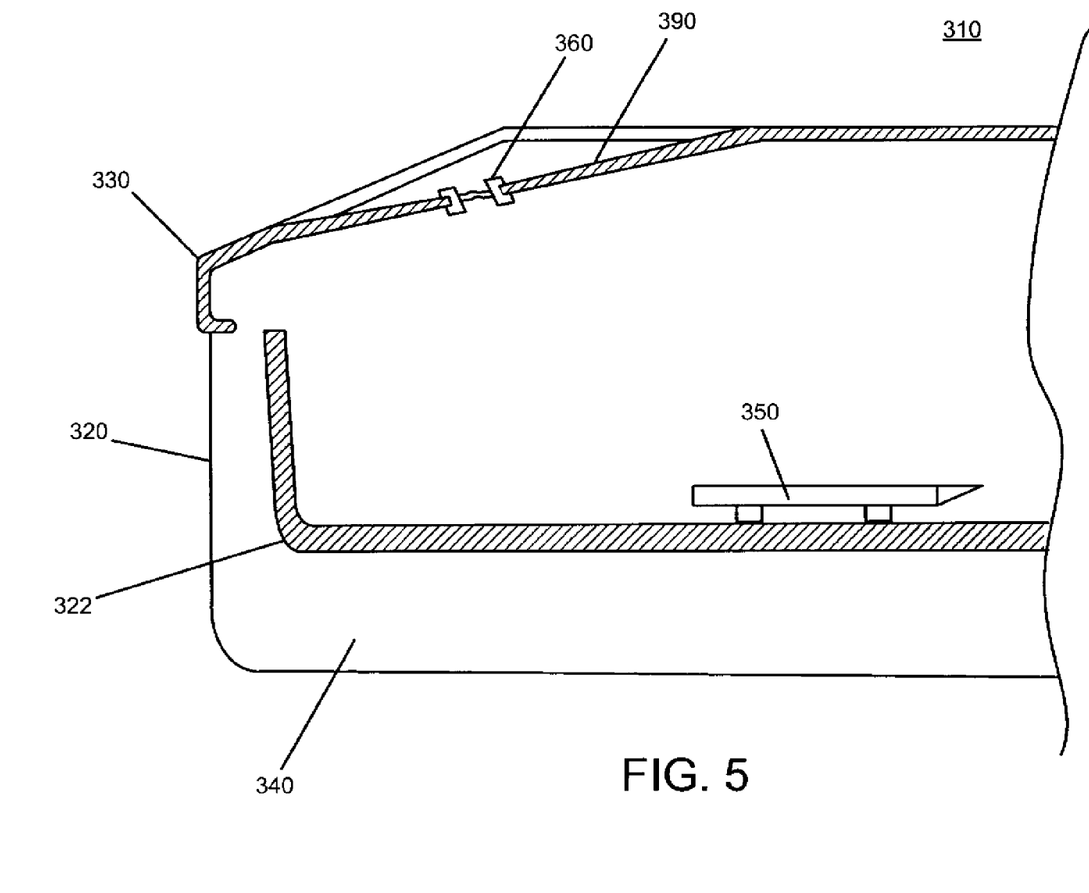
FIG. 5 is a cross-sectional illustration of an apparatus for indicating biological content within a container, in accordance with a fourth exemplary embodiment of the present disclosure.

FIG. 5 is a cross-sectional illustration of an apparatus for indicating biological content within a container 310, in accordance with a fourth exemplary embodiment of the present disclosure. The apparatus for indicating biological content within a container 310 of the fourth exemplary embodiment, which may be referred to herein simply as 'apparatus 310' may be substantially similar to apparatus 10, 110, and 210 of the first, second, and third exemplary embodiments, respectively, and include any of the features, designs and/or configurations that are described with respect to the first or second exemplary embodiments. As is illustrated, the apparatus 310 includes a medical sterilization container 320 having a cover 330 that is removably attached to the medical sterilization container 320. An enclosable, sterilizable interior compartment 340 is formed by the medical sterilization container 320 and the cover 330. The interior compartment 340 is sized to house at least one medical instrument 350, which may be positioned on or supported by a tray 322.

The apparatus 310 also includes an angled mounting portion 390 within the cover 330. The angled mounting portion 390 may be positioned on the cover 330 to contact the biological indicator 360, such as when the biological indicator 360 is formed within the angled mounting portion 390. For example, in FIG. 5, the biological indicator 360 is illustrated as a pressure indicator embedded within the angled mounting portion 390, where the pressure indicator changes shapes based on a temperature within the interior compartment 340. The angled mounting portion 390 may be sized to drain a quantity of condensate away from the biological indicator 360. This may be necessary in sterilization conditions with substantially moist atmospheres, such as in autoclaves using heater water or other heated fluids to sterilize the medical instruments 350. During the sterilization process, the moisture from the sterilization materials may build up on the cover 330 and condense over the biological indicator 360. The angled mounting portion 390 may provide an angled surface within the cover 330 that allows any condensate to drain away from the biological indicator 360 and any other components positioned on the cover 330.

Figure 6:
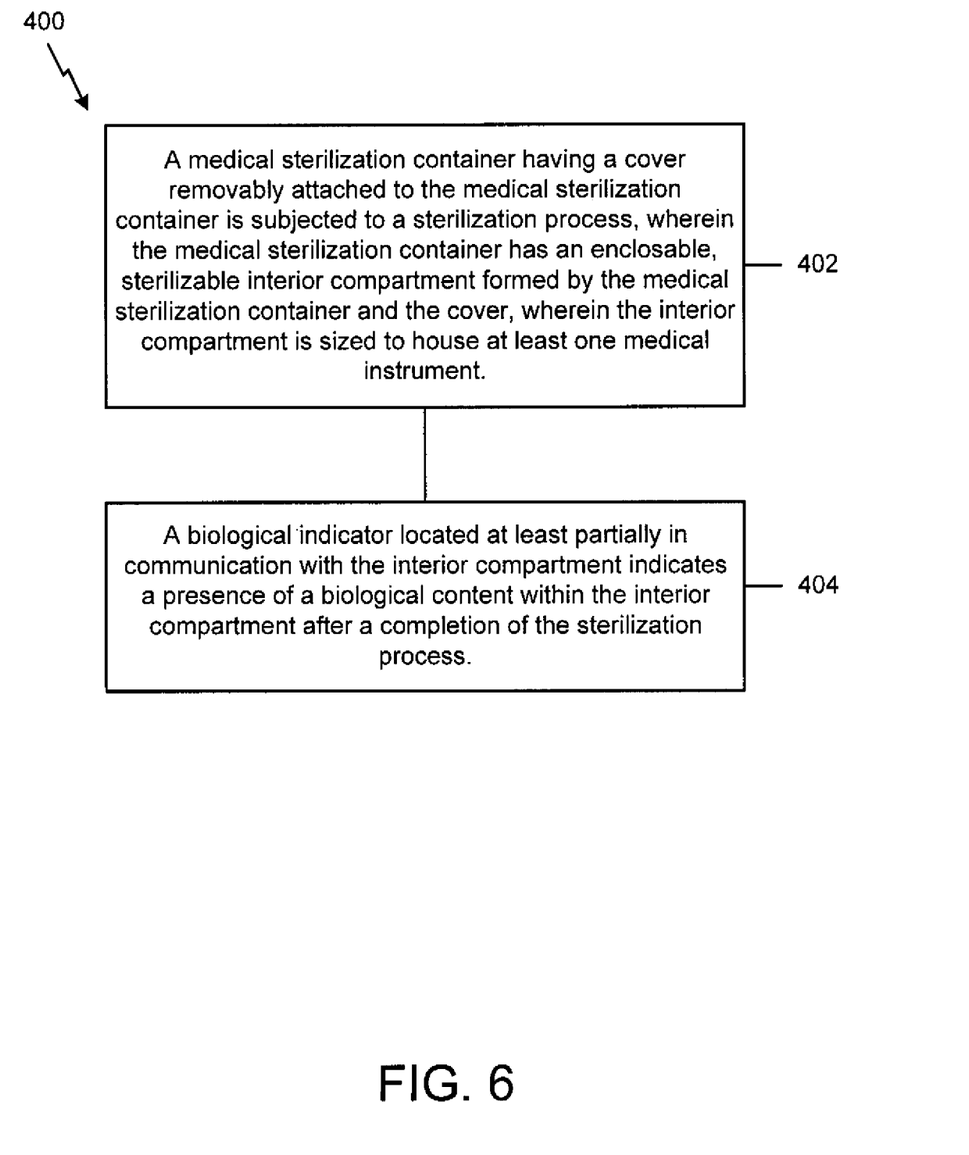
FIG. 6 is a flowchart illustrating a method of indicating biological content within a container, in accordance with the first exemplary embodiment of the present disclosure.

FIG. 6 is a flowchart 400 illustrating a method of indicating biological content within a container, in accordance with the first exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 402, a medical sterilization container having a cover removably attached to the medical sterilization container is subjected to a sterilization process, wherein the medical sterilization container has an enclosable, sterilizable interior compartment formed by the medical sterilization container and the cover, wherein the interior compartment is sized to house at least one medical instrument. A biological indicator located at least partially in communication with the interior compartment indicates a presence of a biological content within the interior compartment after a completion of the sterilization process (block 404).

Of course, the method may include a number of additional steps and variations, including any of the steps, processes, or functions described with respect to FIGS. 1-5. For example, the biological indicator may be positioned fully and/or partially within the interior compartment, and/or in a location viewable from a position external to the interior compartment when the cover is attached to the medical container. The biological indicator may indicate the presence of a biological content by a change in temperature while the biological indicator is viewable from a position external to the interior compartment when the cover is attached to the medical container. For example, the biological indicator may indicate the presence of a biological content with a pressure indicator positioned within at least one of the cover and a wall of the medical sterilization container between the interior compartment and an exterior atmosphere, wherein the pressure indicator deforms shape during a pressure change within the interior compartment. When this occurs, a colored membrane having a first color may be contacted to the pressure indicator to produce a second color.

The biological indicator may also include an electronic-base indicator, such as an electronic sterility indicator at least partially located within the interior compartment. Accordingly, the electronic sterility indicator may indicator the presence of a biological content by monitoring the biological content within the interior compartment and recording a quantity data corresponding to at least one of the monitored biological content, the sterilization process, and a characteristic associated with the sterilization process. The recorded quantity of data may be communicated to the at least one monitored biological content to a receiver. Any number of additional steps, including those not explicitly discussed herein, may be included with the method.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. An apparatus for indicating biological content within a container, the apparatus comprising:
    a medical sterilization container having a cover removably attached to the medical sterilization container;
    a pressurizable, enclosable, sterilizable interior compartment formed by the medical sterilization container and the cover, wherein the interior compartment is sized to house at least one medical instrument; and
    a pressure-activated biological indicator affixed within at least one of the cover and a wall of the medical sterilization container and in communication between both the interior compartment and an atmosphere exterior of the medical sterilization container, wherein after the medical sterilization container has been subjected to a sterilization process and after the atmosphere exterior of the medical sterilization container is substantially at an atmospheric level, the pressure-activated biological indicator provides at least one indication of biological content within the interior compartment.

2. The apparatus for indicating biological content within a container of claim 1, further comprising a materially translucent portion within the cover, wherein an additional biological indicator is viewable through the materially translucent portion from a position external to the interior compartment when the cover is attached to the medical container.

3. The apparatus for indicating biological content within a container of claim 1, further comprising a biological indicator strip positioned fully within the interior compartment.

4. The apparatus for indicating biological content within a container of claim 1, further comprising a biological indicator label positioned fully within the interior compartment.

5. The apparatus for indicating biological content within a container of claim 1, further comprising an additional biological indicator, wherein the additional biological indicator further comprises an indicator label, wherein the indicator label is activated by a change in temperature, wherein the indicator label is viewable from a position external to the interior compartment when the cover is attached to the medical container.

6. The apparatus for indicating biological content within a container of claim 1, wherein the pressure-activated biological indicator deforms shape during a pressure change within the interior compartment.

7. The apparatus for indicating biological content within a container of claim 6, wherein the pressure-activated biological indicator contacts a colored membrane having a first color, wherein a second color is produced when the pressure-activated biological indicator contacts the colored membrane.

8. The apparatus for indicating biological content within a container of claim 1, further comprising an additional biological indicator, wherein the additional biological indicator further comprises an electronic sterility indicator at least partially located within the interior compartment.

9. The apparatus for indicating biological content within a container of claim 8, wherein the electronic sterility indicator monitors the biological content within the interior compartment and records a quantity data corresponding to at least one of the monitored biological content, the sterilization process and a characteristic associated with the sterilization process.

10. The apparatus for indicating biological content within a container of claim 9, wherein the characteristic associated with the sterilization process includes at least one of a sterilization process temperature and a sterilization process duration.

11. The apparatus for indicating biological content within a container of claim 1, further comprising an angled mounting portion within the cover, wherein the pressure-activated biological indicator is mounted proximate to the angled mounting portion, and wherein the angled mounting portion is sized to drain a quantity of condensate away from the pressure-activated biological indicator.

12. The apparatus for indicating biological content within a container of claim 1, wherein the pressure-activated biological indicator further comprises a flexible membrane, wherein the flexible membrane is deformed when a pressure level of the pressurizable, enclosable, sterilizable interior compartment is greater than the atmosphere exterior of the medical sterilization container.

13. A method for indicating biological content within a container, the method comprising the steps of:
    subjecting a medical sterilization container having a cover removably attached to the medical sterilization container to a sterilization process, wherein the medical sterilization container has a pressurizable, enclosable, sterilizable interior compartment formed by the medical sterilization container and the cover, wherein the interior compartment is sized to house at least one medical instrument; and
    indicating a biological content within the pressurized, enclosable, sterilizable interior compartment with a pressure-activated biological indicator affixed within at least one of the cover and a wall of the medical sterilization container and in communication between both the interior compartment and an atmosphere exterior of the medical sterilization container after a completion of the sterilization process and after the atmosphere exterior of the medical sterilization container is substantially at an atmospheric level.

14. The method for indicating biological content within a container of claim 13, further comprising the step of affixing the biological indicator in a location within the cover that allows it to be viewable from a position external to the interior compartment when the cover is attached to the medical container.

15. The method for indicating biological content within a container of claim 13, further comprising the step of positioning an additional biological indicator fully within the interior compartment.

16. The method for indicating biological content within a container of claim 13, further comprising the step of indicating with an additional biological indicator the presence of a biological content by a change in temperature, wherein the additional biological indicator is viewable from a position external to the interior compartment when the cover is attached to the medical sterilization container.

17. The method for indicating biological content within a container of claim 13, wherein the step of indicating a biological content within the pressurized, enclosable, sterilizable interior compartment with the pressure-activated biological indicator further comprises the step of contacting a colored membrane having a first color with the pressure-activated biological indicator, thereby producing a second color when the pressure-activated biological indicator contacts the colored membrane.

18. The method for indicating biological content within a container of claim 13, further comprising the step of indicating with an additional biological indicator the presence of a biological content with a an electronic sterility indicator at least partially located within the interior compartment.

19. The method for indicating biological content within a container of claim 18, wherein the step of indicating with the additional biological indicator the presence of a biological content with a an electronic sterility indicator further comprises the steps of:
    monitoring the biological content within the interior compartment;
    recording a quantity data corresponding to at least one of the monitored biological content, the sterilization process, and a characteristic associated with the sterilization process; and
    communicating at least a portion of the quantity of data corresponding to the at least one monitored biological content to a receiver.

20. The method for indicating biological content within a container of claim 13, wherein pressure-activated biological indicator further comprises a flexible membrane, wherein the step of indicating a biological content within the pressurized, enclosable, sterilizable interior compartment with the pressure-activated biological indicator further comprises the steps of:
    deforming the flexible membrane to a deformed state during the sterilization process; and retaining the flexible membrane in the deformed state after completion of the sterilization process and after the atmosphere exterior of the medical sterilization container is substantially at an atmospheric level.

* * * * *